US00PP20478P3

(12) United States Plant Patent

Maillard et al.

(10) Patent No.: US PP20,478 P3

(45) Date of Patent: Nov. 17, 2009

(54) PEACH TREE NAMED 'FLATPRINCESSE'

(50) Latin Name: *Prunus persica*
Varietal Denomination: FLATPRINCESSE

(75) Inventors: Laurence Maillard, Elne (FR); Arsene Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 199 days.

(21) Appl. No.: 11/434,798

(22) Filed: May 17, 2006

(65) Prior Publication Data

US 2006/0265796 P1 Nov. 23, 2006

(30) Foreign Application Priority Data

May 18, 2005 (EP) ..... 2005/0903

(51) Int. Cl.
*A01H 5/00* (2006.01)

(52) U.S. Cl. ..... Plt./195

(58) Field of Classification Search ..... Plt./195
See application file for complete search history.

(56) References Cited

U.S. PATENT DOCUMENTS

| | | | | |
|---|---|---|---|---|
| PP17,182 | P3 * | 11/2006 | Rubio | Plt./195 |
| 2006/0265795 | P1 * | 11/2006 | Maillard et al. | Plt./195 |
| 2006/0265796 | P1 * | 11/2006 | Maillard et al. | Plt./195 |
| 2006/0265797 | P1 * | 11/2006 | Maillard et al. | Plt./195 |

OTHER PUBLICATIONS

UPOV ROM GTITM Computer Datbase, GTI Jouve Retrieval Software 2007/04 Citations for 'FLATPRINCESSE'.*

* cited by examiner

*Primary Examiner*—Wendy C Haas
(74) *Attorney, Agent, or Firm*—Westerman, Hattori, Daniels & Adrian, LLP.

(57) ABSTRACT

A new and distinct variety of flat peach tree, denominated 'FLATPRINCESSE', has a very high regular productivity and has the same good fruit quality as other varieties: 'MAILLARFLAT' 'FLATPRETTY' 'FLATQUEEN' 'FLATNICE'.

2 Drawing Sheets

This application claims priority of Community plant variety right No. 2005/0903 filed on May 18, 2005 which is hereby incorporated by reference in its entirety.

Botanical classification: *Prunus persica* L. Batsch—White Flat peach.

Variety denomination: 'FLATPRINCESSE'.

BACKGROUND OF THE VARIETY

The present invention relates to a new and distinct variety of *Prunus persica* L. Batsch white flat peach tree. This new tree, named 'FLATPRINCESSE', produces very long lifetime, good eating quality, semi-freestone flesh fruit for fresh market in August in the 66 —Pyrénées Orientales departement—France. Contrast is made to 'MAILLARFLAT' flat peach, standard varieties, for reliable description. 'FLATPRINCESSE' is a promising candidate for commercial success in that it has a very high regular productivity and has the same well fruit quality as other varieties: 'MAILLARFLAT' (unpatented), 'FLATPRETTY' (pending U.S. Plant Pat. application No.11/434,796), 'FLATQUEEN' (pending U.S. Plant Pat. application No.11/434,799) and 'FLATNICE' (unpatented).

ORIGIN OF THE VARIETY

'FLATPRINCESSE' flat peach tree originated in a cultivated area of the south of France, in the 66 —Pyrénées Orientales department—France where it was tested. This place is under a Mediterranean climate in a temperate area characterized by irregular and low precipitation with drought in summer, high temperatures all year long.

The 'FLATPRINCESSE' variety was obtained by open-pollination of the 'MAILLARFLAT' (unpatented) variety. 'FLATPRINCESSE' was provisionally designated and tested as 02.03.21 PBPL and is registered at the Official Catalogue of the Agriculture Ministry of the French Republic December 29, 2004 under number 1016569. It was obtained from open-pollination and is propagated by grafting. It has been determined to have unique tree and fruit characteristics making it worthy for commercial fresh fruit production. There are no known effects of standard rootstock on this scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées Orientales, France.

SUMMARY OF THE VARIETY

The new and distinct variety of 'FLATPRINCESSE' flat peach tree blooms in March at Perpignan in the Pyrénées Orientales departement, France. More particularly, it blooms at the same time as the MAILLARFLAT variety, between 7th and 21st of March.

The first fruit of 'FLATPRINCESSE' ripens in August, 18 days after 'MAILLARFLAT'. More particularly, it approximately ripens between August 16th and 25th

DESCRIPTION OF THE DRAWINGS

In the accompanying drawing, which are as nearly true as it is reasonably possible to make in a colour illustration of this type.

DETAILED BOTANICAL DESCRIPTION

Figure 1:
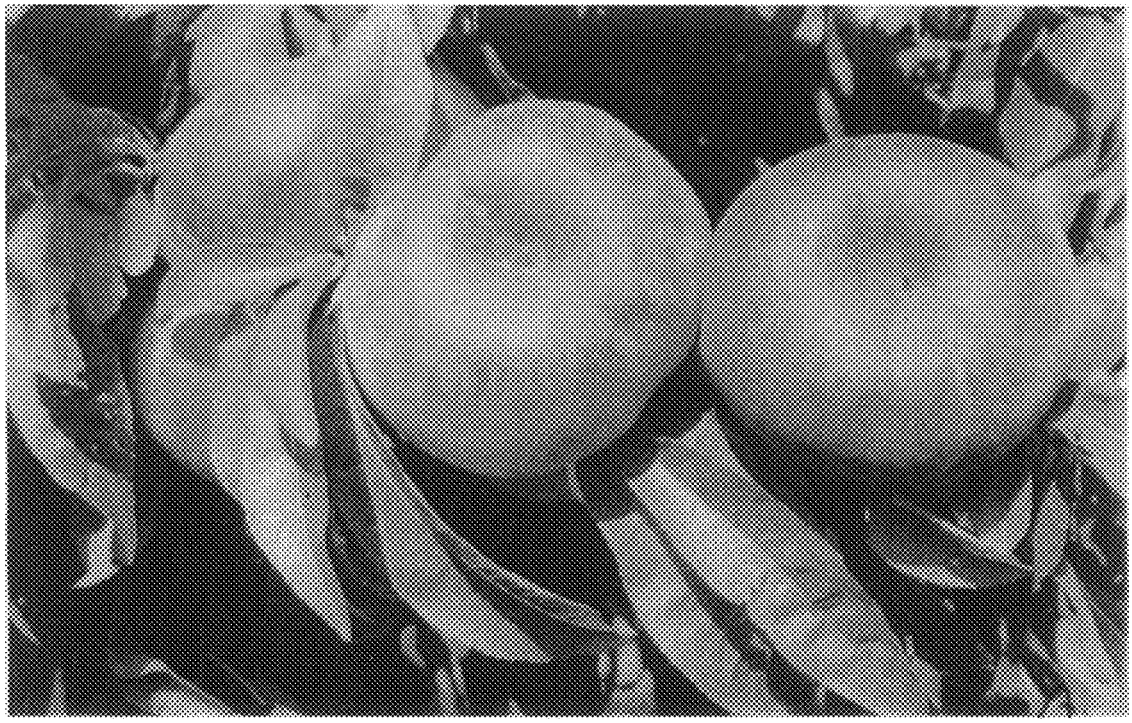
FIG. 1 is a colour photograph which shows the flesh of the fruit of the new variety 'FLATPRINCESSE'.
Figure 2:
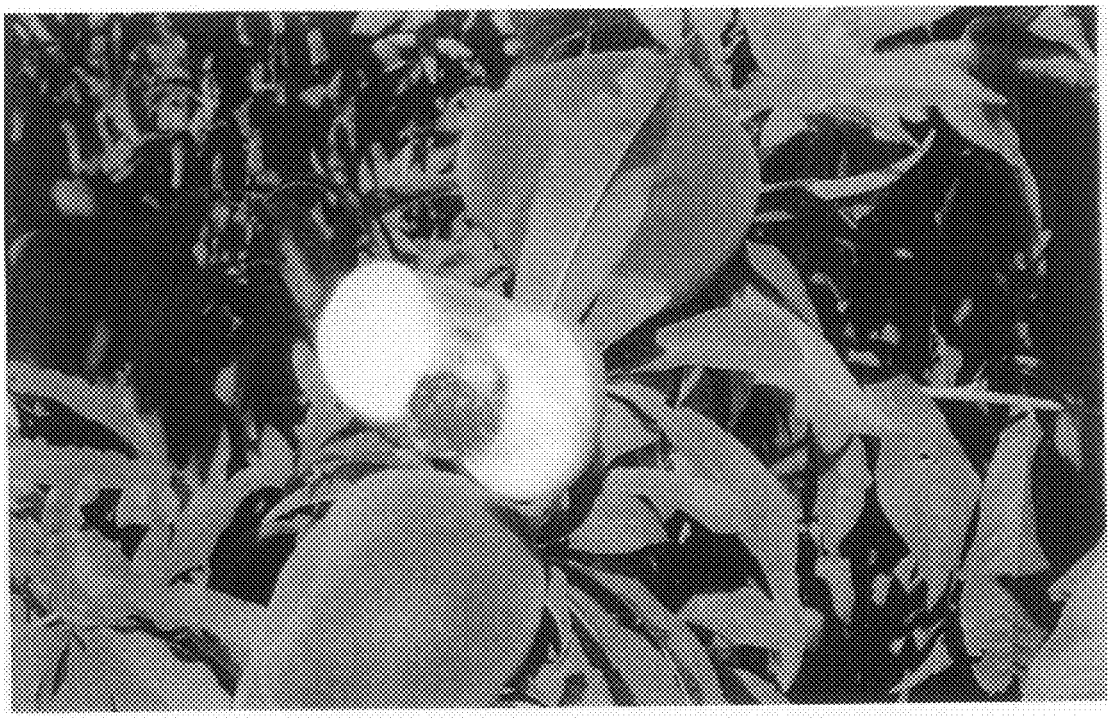
FIG. 2 is a colour photograph which shows a typical specimen of the fruit of the new variety 'FLATPRINCESSE'.

The tree, flowers, and fruit may vary in slight detail due to variations in soil type, cultural practices, and climatic condition. The potential for commercial production of fresh fruit by 'FLATPRINCESSE' is high, due to its fruit early ripening, and fruit evenness of maturity.

Trees are very vigorous and medium stature half-standing in a semi-upright out aspect. The flowering shoot is present excluding brushwoods side away from sun. Flowering begins semi-late in springtime. The type of flower is with relative medium petal size. Petals are Medium Pink. Three or four leaf glands are present and reniform. Time of maturity for consumption is late. The fruit flesh is white and its skin present a red-blush color. The stone is small size and the flesh is semi-clingstone.

Compared to 'MAILLARFLAT' variety, 'FLATPRINCESSE' has an older time of maturity, 18 days later. Fruits are red coloured until over 90% of their skin instead of 60 to 70% for 'MAILLARFLAT' fruits. 'FLATPRINCESSE' presents more flowers, 45 flowers per meter instead of 40 flowers per meter for 'MAILLARFLAT'. 'FLATPRINCESSE' fruit tastes the same as 'MAILLARFLAT', semi sweet and aromatic, although evenness of productivity is better and regular.

DETAILED DESCRIPTION

Referring more specifically to the pomological details of this new and distinct variety of flat peach tree, the following has been observed, if not differently specified, during the second fruiting season under the ecological conditions prevailing at the orchards located in Elne, in the Pyrénées Orientales departement, France. All observations have been done on rootstock cultivar. The rootstock was a 'Franc Inra Montclar®' (unpatented) tree. All major color code designations are by reference to The R.H.S. Color Chart (Fourth Edition) provided by The royal Horticultural Society of Great Britain.

TREE

Size:

*Generally.*—Considered medium to large as compared to other common commercial flat peach cultivars ripening in the middle season of maturity. The tree size the first year was approximately 280 cm. The tree was pruned during each following dormant season to a height of approximately 250 cm. Current season shoots growth could reach 80 cm. So the tree size from the second year (second and next years) reached a final height of 330 cm with current season shoots length comprised.

Spread: Approximately 200 cm with a cylindrical shape. The whole orchard was oriented to a central leader organisation, with tree lines spaced of 4.0 meters and trees spaced of 1.0 meter in a same tree line. As a result, the orchard contains 2500 trees by hectare.

Vigor: Considered very vigorous.

Productivity: Very Productive. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

Bearer: Very regular. Fruit set has been heavy during the years of observation and thinning of 1 fruit on 3 was useful every year during the past 5 years. Fruit have an important magnifying potential.

Form: The 'FLATPRINCESSE' variety has naturally a semi-upright shape.

Density: Considered dense.

Hardiness: The present tree was grown and evaluated in France. The variety appears to be hardy under typical central Pyrénées Orientales departement climatic conditions. Experimentations on different sites with winter chilling requirement comprised between 350 and 1200 hours showed a good behavior of the tree in all cases. Ascertained temperatures as low as −12 degrees Celsius caused no damages to the tree. The tree was also very resistant to frosty springtime weather.

TRUNK

Diameter: Approximately between 7.0 and 8.0 cm in diameter when measured at a distance of approximately 30 cm above the soil level.

Bark texture: Considered slightly rough, with folds of papery scarfskin being present.

Lenticels: Numerous lenticels are present. The lenticels range in size from approximately 0.5 cm in width, and from 0.1 to 0.2 cm in height.

Lenticel colour: The outside of lenticels has a silver-grey color (varying from RHS Grey 201 D to RHS Black 202 D), whereas the inside is considered brown (RHS Greyed Orange 166B).

Bark colouration: The bark has a silver-grey color a little darker than the lenticels (varying from RHS Grey 201 C to RHS Black 202 C).

BRANCHES

Size: Mature branches as well as current season shoots are medium to thick for the variety.

Diameter: Average as compared to other flat peach varieties. The current season shoots have a diameter from 4.0 to 12.0 millimeters, and branches of trees have a diameter comprised between 22.0 and 30.0 millimeters.

Surface texture: Average, wood which is several years old has no furrowed appearance.

Crotch angles: Primary branches are considered variable, but the crotch angles are generally around 70 degrees from the horizontal axis. This particular characteristic is not considered distinctive of the variety, however.

Current season shoots:

*Surface texture.*—Substantially glabrous.

Internode length: Generally 22.0 to 30.0 millimeters.

Colour of mature branches: Medium grey-brown (varying from RHS Grey Brown 199 C to B).

Current seasons shoots:

*Colour.*—The color of new shoot tips is considered a light green (varying from RHS Green 143 C to D) on lower part of new shoot tips, whereas the upper part is colored in reddish brown (varying from RHS Greyed Red 182 B to C), darkening when more exposed to the sun.

LEAVES

Size: Considered large for the species. Leaf measurements have been taken from vigorous, upright, current-season growth at approximately mid-shoot. The ratio leaf length/leaf width is around 4.

Leaf length: Approximately 170 to 190 millimeters without the petiole.

Leaf width: Approximately 40 to 50 millimeters.

Leaf base shape: Concave.

Leaf form: Lanceolate.

Leaf tip form: Acuminate and small.

Leaf colour:

*Upper leaf surface.*—Dark Green (RHS Green 137 A).

*Lower surface.*—Medium Green (varying from RHS Green 137 B to 137 C).

Leaf texture: Smooth and glabrous.

Leaf venation: Pinnately veined.

Mid-vein:

*Colour.*—Light yellow green (RHS Yellow Green 145 D).

Leaf margins: Slightly undulating.

Form: Considered slightly dentate.

Uniformity: Leaves are isolated or grouped by 2 or 3. In this last case, it is found one leaf of normal size with one or two smaller leaves (size-reduction of 50 % and more).

Leaf glands:

*Size.*—Considered medium to large, between 1.5 and 2.0 millimeters.

*Number.*—Generally between 3 and 4.

*Type.*—Reniform.

*Colour.*—On young leaves, leaf glands color is considered a pale green (RHS Green 145 B). On older leaves, leaf glands color turns to a dark brown (varying from RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

*Generally.*—Observations have been made at the end of blooming, on March 2, 2008.

Flower buds:

*Generally.*—At pre-floral stage of development, the floral buds are conic in form with a round tip. Their form is evolving until blooming, with variables dimensions. Just before blooming, floral buds are approximately 10.0 millimeters wide and approximately 18.0 millimeters long.

Flower buds:

*Colour.*—This characteristic is dependent upon the proximity to bloom. At pre-floral stage of development, the bottom of the flowers buds, formed by sepals, is of purple- brown color (RHS Greyed Purple 183 A); the corolla, formed by petals, is generally of pale pink color (varying from RHS Red Purple 65 A to B). Petals color shows an evolution until the end of flowering. The buds are considered hardy under typical central Pyrénées Orientales departement climatic conditions.

Hardiness: No winter injury was noted during the last several years of evaluation in the central Pyrénées Orientales departement, with winter temperatures as low as −12 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally March. The first bloom, observed on Feb. 26, 2002, was exceptionally early. Second and third bloom took place respectively on March 10, 2003 and Mar. 7, 2004.

Blooming time: Considered early-season in relative comparison to other commercial nectarine cultivars grown in the Pyrénées-Orientales departement, France. The date of full bloom is observed on March, more particularly between March 3th and 18th. The date of bloom varies slightly with climatic conditions and cultural practices.

Duration of bloom: Approximately 15 days. This characteristic varies slightly with the prevailing climatic conditions.

Flower type: The variety is considered to have a showy type flower.

Flower size: Considered large. Flower diameter at full bloom is approximately 32.0 to about 37.0 millimeters.

Bloom quantity: Considered abundant, approximately about 45 flowers per meter.

Flower bud frequency: Generally 2 flower buds appear per node, occasionally 1.

Petal size:

*Generally.*—Considered medium for the species.

Length: Generally about 18.0 millimeters.

Width: Generally about 15.6 millimeters.

Petal form: Rounded.

Petal count: 5.

Petal texture: Smooth and glabrous.

Petal colour: Medium Pink (RHS Red Purple 65 B) when young, darkening with advancing senescence.

Fragrance: Slight.

Petal claw:

*Form.*—The claw is considered to have a conic form with a slighty rounded extremity.

*Length.*—Approximately 5.0 to 6.0 millimeters.

*Width.*—Approximately 4.0 to 5.0 millimeters.

Petal margins: Generally very slightly undulated.

Petal apex:

*Generally.*—The petal apices are generally entire at the tip, dome-shaped.

Flower pedicel:

*Length.*—Considered medium-long and having an average length of approximately 3.0 to 4.0 millimeters.

*Diameter.*—Considered average, approximately 2.0 millimeters.

*Colour.*—Brown to Light Brown (varying from RHS Grey Brown N199 C to D).

Floral nectaries:

*Colour.*—A greenish yellow (ranging from RHS Yellow Group 13 A to B to RHS Yellow Green 150 A to B).

Calyx:

*Internal surface texture.*—Smooth and glabrous.

*Color.*—The outer surface of the calyx is considered of Purple-brown (RHS Greyed Purple 183 A) color.

Sepals:

*Surface texture.*—The outer surface has a short, fine pubescent texture.

*Size.*—Average.

*Colour.*—A Purple-brown (RHS Greyed Purple 183 A).

Average number of stamens per flower: Approximately 40 stamens per flower.

Anthers:

*Generally.*—Average in length.

*Color.*—Orange-Yellow (varying from RHS Yellow Orange 16 A to B). Anthers are becoming brown after maturity (RHS Greyed Purple Group 178 A).

Pollen production: Pollen is abundant, and has a yellow color (varying from RHS Yellow Orange 17 B to C). The present variety is considered self fruitful (self-pollinating).

Filaments:

*Size.*—Variable in length, approximately 11.0 to 18.0 millimeters in length. In all cases filament's length is superior or equal to pistil's length.

Color: Considered light pink (varying from RHS Red Purple 62 C to D) to darker pink (varying from RHS Red Purple 73 A to B) with advancing senescence.

Pistil:

*Number.*—Generally 1.

*Generally.*—Average in size.

*Length.*—Approximately 12.0 to 15.0 millimeters including the ovary; Smaller or equal to filament's length.

*Colour.*—Considered a very pale green (varying from RHS Yellow Green 150 D Group to RHS Yellow Green 151 D Group).

*Surface texture.*—The variety has a glabrous pistil.

FRUIT

Maturity when described: Very firm ripe condition (shipping ripe).

Date of first picking: Aug. 16, 2002. The date of harvest varies slightly with the prevailing climatic conditions.

Date of last picking: Aug. 23, 2002, only 2 harvests were necessary.

Size:

*Generally.*—Considered large, and uniform.

Average cheek diameter: Approximately 70.0 to 80.0 millimeters

Average axial diameter: Approximately 37.0 to 45.0 millimeters

Typical weight: Approximately between 150.0 and 200.0 grams. This characteristic is high dependent upon the prevailing cultural practices, and therefore is not particularly distinctive of the variety.

Fruit form:

*Generally.*—Flat and rounded. The fruit is generally uniform in symmetry, viewed from pistil end.

Fruit suture: Shallow, extending from the base to the apex. No apparent callousing or stitching exists along the suture line.

Suture:

*Colour.*—This has generally a color similar to the blush fruit color, an Orange Red (varying from RHS Orange Red Group 34 A to B).

Ventral surface:

*Form.*—Smooth.

Apex: Depressed.

Base: Shallow.

Stem cavity: Average depth of the stem cavity is about 0.5 to 0.6 cm. Average width is about 1.2 to 1.5 cm.

Fruit skin:

*Thickness.*—Considered thick and strong, and very tenacious to the flesh to tenacious to the flesh depending on stage of maturity.

*Texture.*—Slightly pubescent.

*Taste.*—Semi-sweet.

*Tendency to crack.*—Generally not observed.

Colour:

*Blush colour.*—This blush colour is generally homogenous and Orange Red (varying from RHS Orange Red Group 34 A to B). The red blush covers between 80% and 90% of the fruit skin surface. The percentage of the blush on the fruit skin surface can vary, and is generally dependant upon the prevailing conditions under which the fruit was grown.

*Ground colour.*—Yellow Orange (RHS Yellow Orange Group 18 D).

Fruit stem: Medium in length, approximately between 4.0 and 5.0 millimeters.

Diameter: Approximately between 3.0 and 4.0 millimeters.

Colour: Pale green (varying from RHS Yellow Green 145A to 145 B).

Flesh:

*Ripens.*—Very evenly, homogenous, long shelf-life of the fruit.

*Texture.*—Very firm, very dense, juicy at harvest maturity stage.

*Fibers.*—Generally none observed.

*Aroma.*—Pronouced.

*Eating quality.*—Considered very good, aromatic.

*Flavor.*—Considered semi-sweet. The Brix is superior to 13.0 degrees. Acidity is comprised between 6 and 9 meq/100ml. The flavor is considered aromatic. The flesh is juicy.

*Juice.*—Jucy to very juicy at complete maturity.

*Brix.*—Generally superior to 13.0 degrees. This characteristic varies slightly with the number of fruit per tree; prevailing cultural practices; and the surrounding climatic conditions, and can be much more higher.

*Flesh colour.*—White (RHS White Group N155D) with a slight red pigmentation under the skin and close to the stone.

STONE

Type: Semi-clingstone.

Size: Considered small for the variety.

Length: Approximately between 20.0 and 25.0 millimeters.

Width: Approximately between 20.0 and 24.0 millimeters.

Diameter: Approximately between 12.0 and 15.0 millimeters.

Form: Flat.

Base: Straight.

Apex:

*Shape.*—The stone apex has a flat tip.

Stone Cavity: Considered small size, with dimensions corresponding to stone's dimensions.

Stone surface:

*Surface texture.*—The pit is transversely furrowed on its entire surface. Furrows are more pronounced and more flat toward lateral faces.

*Ridges.*—The surface texture is generally characterized by more prominent ridges along the ventral edges and is more prominent at the apical tip.

Ventral edge:

*Width.*—Considered small.

Dorsal edge:

*Shape.*—Grooved.

Stone colour: The color of the dry stone is generally considered an Orange to Red Brown (varying from RHS Greyed Orange 173 C to D).

Tendency to split: Splitting is absent or very low, depending on climatic conditions between blooming period and stone hardening.

Kernel:

*Size.*—The kernel is considered small.

*Length.*—About 7.0 millimeters.

*Thickness.*—About 5.0 millimeters.

*Form.*—Considered flat and and elliptic.

*Pellicle.*—Pubescent.

*Colour.*—The kernel skin is a light yellowish orange (RHS Greyed Orange 166 C). The almond is cream-white (RHS Orange Chite 159 D). The kernel and its embryo are mature at the time of fruit maturity.

Use: The subject variety 'FLATPRINCESSE' is considered to be a nectarine tree of the medium season of maturity, and which produces fruit that are considered very firm, attractively coloured. Fruits are excellent for uncooked consumption, crunchy or at full maturity, and very aromatic. They are useful for both local and very long distance shipping, with a shelf life of few weeks after harvest.

Keeping quality: Good. Fruit stayed a little more than one week on tree before harvest and then, has stored well until 2 to 3 weeks after harvest at 2.0 degree Celsius. They have a slow maturation and a long shelf life both on the tree after growth completion and after harvesting without alteration.

Shipping quality: Considered good. The fruit of the new flat peach variety showed minimal bruising of the flesh or skin damage after being subjected to normal harvesting and packing procedures.

Resistance to insects and disease: No particular susceptibilities were noted. The present variety has not been shown to be very sensitive to powdery mildew, or conservation diseases and decay due to its thick and strong skin.

Although the new variety of flat peach tree possesses the described characteristics when grown under the ecological conditions prevailing near the town of ELNE, FRANCE, it should be understood that variations of the usual magnitude and characteristics incident to changes in growing conditions, fertilization, pruning, pest control and horticultural management are to be expected.

We claim:

1. A new and distinct variety of peach tree, as herein illustrated and described.

* * * * *